United States Patent [19]
Jorgenson et al.

[11] Patent Number: 5,269,900
[45] Date of Patent: Dec. 14, 1993

[54] METHOD AND DEVICE FOR HIGH SPEED SEPARATION OF COMPLEX MOLECULES

[75] Inventors: James W. Jorgenson, Chapel Hill, N.C.; Curtis A. Monnig, Riverside, Calif.

[73] Assignee: University of North Carolina at Chapel Hill, Chapel Hill, N.C.

[21] Appl. No.: 581,683

[22] Filed: Sep. 13, 1990

[51] Int. Cl.$^5$ .................... G01N 27/26; G01N 27/447
[52] U.S. Cl. ............................. 204/299 R; 204/180.1
[58] Field of Search .............. 204/180.1, 182.8, 299 R

[56] References Cited

U.S. PATENT DOCUMENTS 4,729,947  3/1988  Middendorf .................... 204/182.8
5,110,431  5/1992  Moring ............................. 204/180.1

OTHER PUBLICATIONS

Annino, Raymond, "Cross–Correlation Techniques in Chromatography", *J. of Chromatographic Science*, 14, 1976, 265–270.
Hirschfeld, T., "Quantum Efficiency Independence of the Time Integrated Emission from a Fluorescent Molecule", *Applied Optics*, 15, Dec. 1976, 3135–39.
Phillips, John B., "Multiplex Gas Chromatography", *Analytical Chemistry*, 52, Apr. 1980, 468–478.
Cheng and Dovichi, "Subattomole Amino Acid Analysis by Capillary Zone Electrophoresis and Laser-Induced Fluorescence", *Science*, 242, 1988, 562–564.
Jorgenson and Lukacs, "Zone Electrophoresis in Open–Tubular Glass Capillaries" *Anal. Chem.* 53, 1981, 1298–1302.
Nelson et al., "Use of Peltier Thermoelectric Devices to Control Column Temperature in High-Performance Capillary Electrophoresis", *J. Chromatography*, 480, 1989, 111–127.
Pentoney, Stephem L., et al., "On-Line Connector for Microcolumns: Application to the On-Column o-Phthaldialdehyde Derivatization of Amino Acids Separated by Capillary Zone Electrophoresis," *Anal. Chem.* 1988, 60, 2625–2629.
Nickerson & Jorgenson, "High Speed Capillary Zone Electrophoresis with Laser Induced Fluorescence Detection," *J. HRC&CC*, 11, 1988, 533–534.
Phillips, John B, "Multiplex Gas Chromotography", *Analytical Chemistry*, 52, Apr. '80, 468–478.
Stephen L. Pentoney, Jr. et al "On–Line Connector for Microcolumns: Application to the On–Column o-Phthaldialdehyde Derivatization of Amino Acids Separated by Capillary Zone Electrophoresis" *Analytical Chemistry* 60 (1988) 2625–2629.

*Primary Examiner*—John Niebling
*Assistant Examiner*—John S. Starsiak, Jr.
*Attorney, Agent, or Firm*—Majestic, Parsons, Siebert & Hsue

[57] ABSTRACT

A device and method useful for high-speed electrophoresis is disclosed. The device includes an on-column optical gating apparatus for high-frequency modulation of sample introduction, a variable resistance capillary, and a high voltage power supply to induce differential migration. The device separates charged molecules, including complex organic compounds, quickly and efficiently. The device can be used in multiplex chromatographic and electrophoretic separations.

22 Claims, 6 Drawing Sheets

| Voltage Drop Across This Portion of the Capillary for a 25 kV Driving Potential | | |
|---|---|---|
| (2.1 kV) | 235 MΩ | 401 (150 μm i.d., 85 cm) |
| (22.7 kV) | 2500 MΩ | 402 (10 μm i.d., 4 cm) |
| (0.2 kV) | 16.5 MΩ | 403 (150 μm i.d., 14 cm) |

METHOD AND DEVICE FOR HIGH SPEED SEPARATION OF COMPLEX MOLECULES

FIELD OF THE INVENTION

This invention relates generally to the fields of electrophoresis and chromatography. More particularly, it concerns an improved process and apparatus for sample introduction and high-speed separation of complex molecules.

The government has rights in this invention, pursuant to NIH Contract GM39515, NSF Contract CHE-8912926 and NSF Postdoctoral Fellowship Program in Chemistry No. CHE-9044317.

BACKGROUND OF THE INVENTION

Electrophoresis has been widely used for several decades as a method for separating ionized compounds. More recently, there has been growing interest in capillary electrophoresis (CE) as a general, high-efficiency means of separating complex mixtures. In CE, the separation is carried out in a capillary tube with a typical inner diameter of 5 to 100 μm and a total length of 30 to 100 cm. The small radial dimensions of the capillary allow Joule heat to be dissipated efficiently, which in turn allows potentials as high as 30 kV to be applied across the length of the capillary. As a result, excellent separation efficiencies (>1,000,000 theoretical plates) have been reported for many compounds, often in analysis times as short as a few minutes When compared with chromatographic separation procedures, CE can offer a significant improvement in both speed and efficiency for the separation of charged species.

With a typical CE instrument, separation of a mixture usually requires between 5 and 30 minutes. Although this time is fast relative to many competitive procedures, it is slow relative to many chemical events. Another problem is that the traditional methods of sample introduction (e.g., electromigration and hydrostatic pressure) are relatively slow and unwieldy. As a result, CE has not been used as a method for monitoring dynamic chemical systems. To gain this capability, it is necessary to increase the speed of the analysis. One method for achieving this goal is to reduce the time required for the electrophoretic separation. This cannot be achieved by simply increasing the potential across the capillary (and maintaining the same capillary length) or by decreasing the length of the capillary (and maintaining the same potential). Increasing the potential leads to excessive Joule heating and decreasing the length of the capillary without increasing the field strength adversely affects resolution.

It is an object of the present invention to provide an improved device and method for increasing the speed of electrophoretic and chromatographic separations. It is another object to provide an improved capillary system wherein an electric field can be concentrated in a particular section of a capillary column. It is a further object to provide a high-frequency sample modulation device that can be employed for multiplex chromatographic and electrophoretic separations.

SUMMARY OF THE INVENTION

The present invention provides an improved high-speed device and method that dramatically increases the speed of analysis of complex molecules with little loss of separation efficiency. In one aspect of the invention, capillaries of different diameters are used to concentrate an electrical field in a particular section of the separation column. This "enhanced" electrical field produces an increase in the electro-osmotic flow and electromigration of charged species which significantly reduces the time for analysis Another aspect of the invention provides an on-column optical sample injection device for high-frequency modulation of sample introduction into a capillary column. This device can also be used for chromatographic analysis as well. Yet another aspect of the invention employs means for applying a substantially continuous stream of analyte to a separation column and means for modulating the analyte supplied so as to render the analyte detectable.

The rapidity with which an analysis can be performed makes the invention particularly well suited for multiplex separations It is expected that because of the small size of the inventive instrumentation, an entire column, for instance, can be readily placed on a single substrate wafer (chip) This would facilitate column handling and permit integrated cooling and heating.

DESCRIPTION OF PREFERRED EMBODIMENTS THEORY

Jorgenson and Lukacs [Anal Chem., 53, 1981, 1298.] previously developed a set of equations which describe the efficiency and speed of capillary electrophoretic separations. These equations are:

$$N = \frac{\mu V_1}{2D} \quad (1)$$

$$t = \frac{L l}{\mu V} \quad (2)$$

where $\mu$ is the effective electrophoretic mobility of the analyte, V is the total applied voltage, $V_1$ is the voltage drop between the point of sample introduction and detection, L is the total length of the capillary in which the separation is being performed, l is the length of the capillary between the point of injection and the point of detection, N is the number of theoretical plates, D is the diffusion constant for the species, and t is the time required for the analyte to migrate to the detector. When discussing high-speed separations, it is desirable to develop a new equation which expresses the number of theoretical plates (N) which can be obtained in a unit period of time (t). This new equation can be derived from the two previous formulas:

$$\frac{N}{t} = \frac{\mu^2 V_1 V}{2 D l L} \quad (3)$$

This expression can be simplified to:

$$\frac{N}{t} = \frac{\mu^2}{2D} \left(\frac{V}{L}\right)^2 \quad (4)$$

Thus, to maximize the number of theoretical plates obtained in any given time, the voltage to length ratio should be maintained at as high a level as possible Nickerson and Jorgenson [HRC&CC, 11, 1988, 533.] demonstrated the utility of elevated V/L ratios by separating 8 amino acids in less that 70 seconds. In practice, what ultimately determines the V/L ratio is Joule heating of the capillary Overheating of the capillary is recognized to produce broadened peaks [Lukacs, dissertation, University of North Carolina at Chapel Hill, 1983]. As this mechanism was not considered in the derivation of equation 4, the relationship between the indicated parameters are likely to change To develop an expression for power dissipation in the capillary, first the current passing through the capillary (i) and the effective resistance of the buffer-filled capillary (R) must be calculated. Equations 5 and 6 allow these values to be defined in terms of fundamental parameters:

$$i = \frac{V \pi r^2}{\rho L} \quad (5)$$

$$R = \frac{\rho L}{\pi r^2} \quad (6)$$

where i is the current passing through the capillary, $\rho$ is specific resistance of the buffer filling the capillary, and r is the radius of the central channel. By substitution, the power dissipation in the capillary can be calculated as shown in equation 7.

$$P = i^2 R = \frac{V^2 \pi r^2}{\rho L} \quad (7)$$

A more useful parameter is the power dissipated per unit length of capillary. Dividing through equation 6 by the column length (L) gives the following expression.

$$\frac{P}{L} = \left(\frac{V}{L}\right)^2 \frac{\pi r^2}{\rho} \quad (8)$$

Interestingly, the ratios N/t and P/L are both proportional to $(V/L)^2$. Thus, for all other factors remaining constant, N/t is proportional to P/L.

As a general rule, for a passively (radiatively) cooled column, a power dissipation of less than 1 Watt per meter of capillary produces negligible broadening of sample zones. It appears that the key to increasing the speed of a CE separation is to establish a set of experimental conditions in which the electric field is maintained at as high a level as possible, but where thermally induced zone dispersion is inconsequential. Equation 7 indicates that the power dissipation may be kept within acceptable limits simply by reducing the radius of the column. Although this procedure is very effective at minimizing power dissipation in the column, it can increase the difficulty of finding a suitable detector to record the passage of the analyte zone. An alternative procedure is to actively thermostat the column to help dissipate the excess heat [Nelson et al., J. Chrom., 408, 1989, 111]. For temperature stabilized capillaries, operation at power levels in excess of the previously stated limits may prove both practical and desirable.

INSTRUMENTATION

Sample Introduction by On-Column Optical Gating

Figure 1:
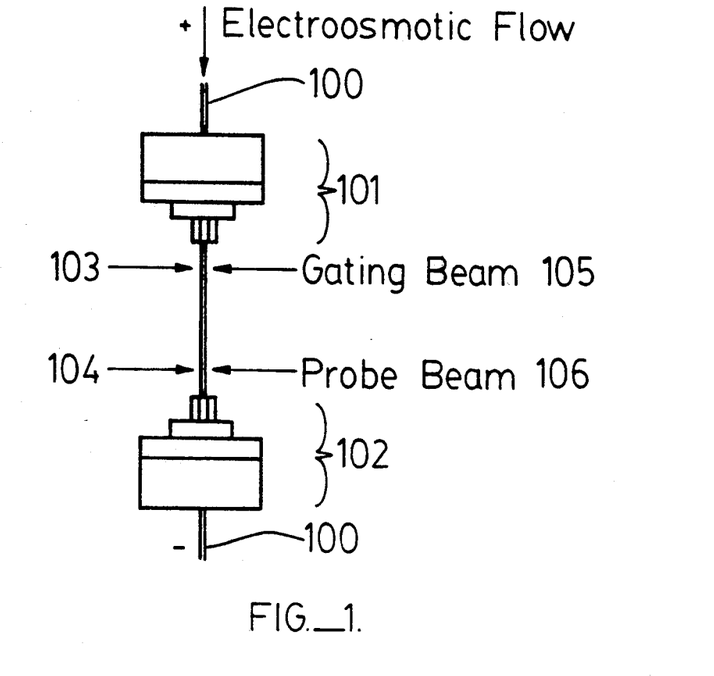
FIG. 1 is a diagram of a capillary mount showing the relative position of the capillary, the "gating" and the "probe" laser beams.
Figure 2:
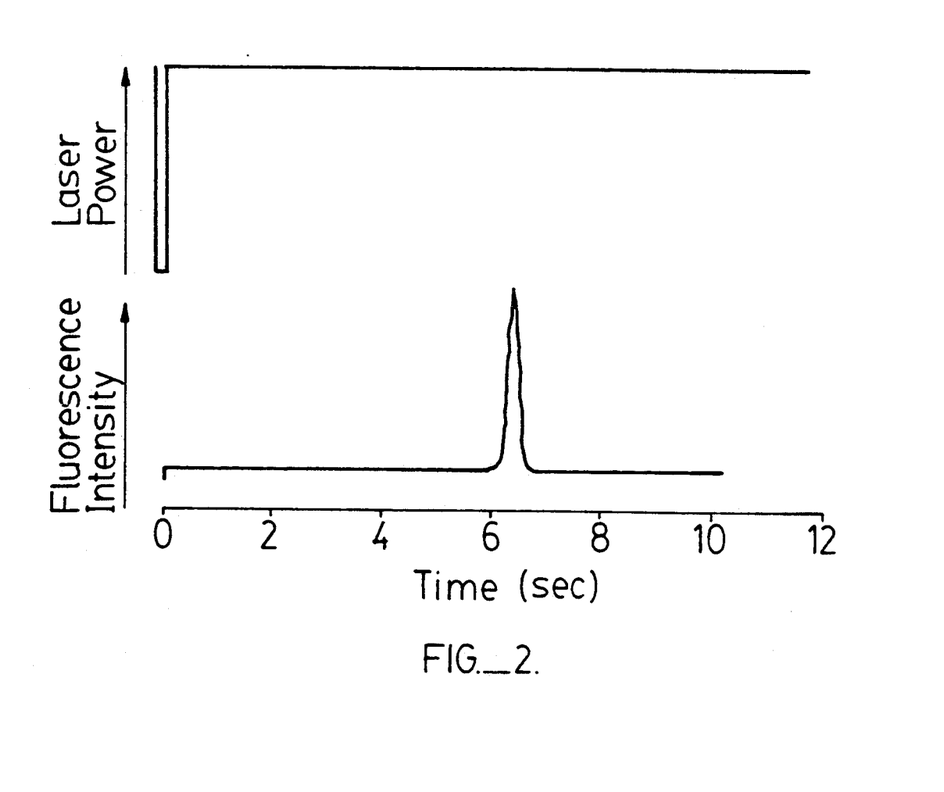
FIG. 2 is a diagram showing the temporal relationship between the intensity of the "gating" beam and the fluorescence signal generated at the "probe" laser beam.

Typically, in most capillary-based separations instruments, the sample is introduced as a "plug" of material at one end of the column and allowed to traverse the column where the separation occurs. With on-column optical gating, the components in the mixture to be determined are first tagged with a fluorescent molecule and then continuously introduced into one end of the column. As shown in FIG. 1, capillary 100 is held in position by capillary supports 101 and 102. The polyimide coating on the portion of the capillary 100 situated between the supports has been removed. Near the entrance of capillary 100, at position 103, a laser (not shown) is used to photodegrade the tag and thus render the material undetectable to a fluorescence detector which is located at position 104 further along the column. Position 103 is referred to as the point of sample gating where gating beam 105 is focused, and position 104, the point of detection, is where probe beam 106 is directed. As will be discussed further below, an advantage of the inventive device is that the distance between the point of sample gating and point of detection can be very short. This distance generally is less than 10 cm, and preferably between 1–5 cm. A sample zone is generated by momentarily preventing the laser from striking the column, and thereby allowing a small amount of tagged material to pass intact. Because the sample modulation is optical rather than mechanical, temporally narrow plugs of material can be formed in the column. Furthermore, the formation occurs while the capillary is maintained at the operating voltage. Separation of the tagged species occurs primarily in the column region between the point of sample gating and the point of detection. Because separation occurs throughout the length of the column between the electrodes, the level of separation of analyte in the narrow plugs formed can be varied depending on where along the column the gating point is chosen. Electrodes from the high potential source are situated in large buffer reservoirs at the ends of each column. Thus, a fluorescence signal will be recorded at the detector channel at some time delay from the interruption of the gating beam This temporal relationship is illustrated in FIG. 2.

On-column optical gating applies equally well to chromatography, especially, for instance, in high speed liquid chromatography separations of complex organic molecules.

Figure 3:
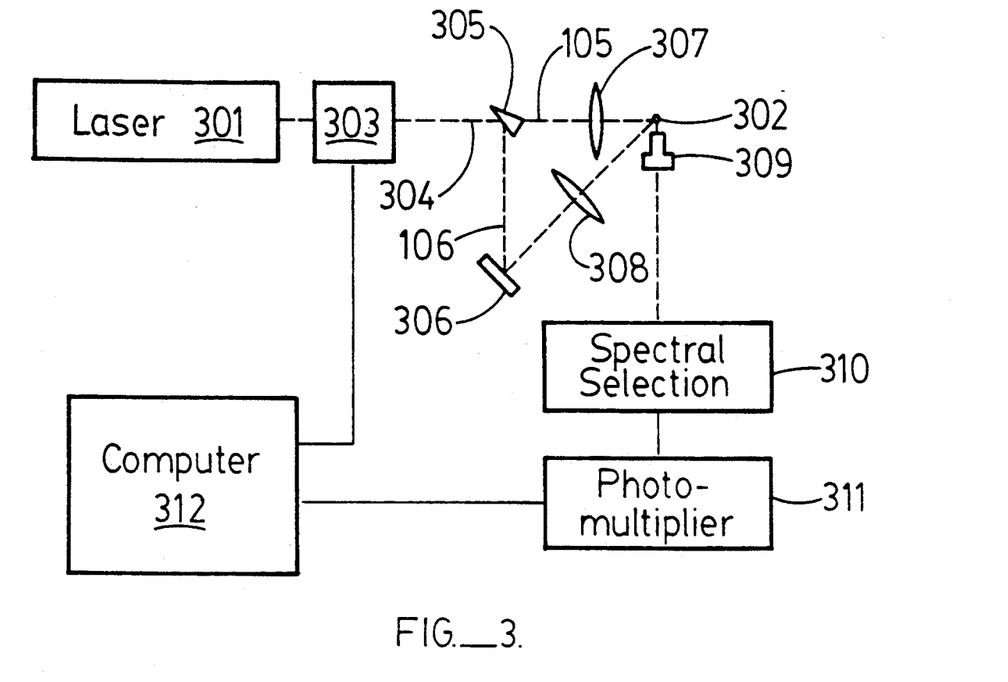
FIG. 3 is a block diagram of a "fast" capillary electrophoresis instrument.

FIG. 3 shows a block diagram of the instrument used for high speed electrophoretic separations. An argon-ion laser 301 (Model 70-2, Coherent Inc.) operating at less than one watt of power at 488.0 nm is focused into the central channel of capillary 302 with a fused silica lens 307 (f.l.=75 mm, Oriel Corporation) to photodegrade the fluorescent species. Intensity modulation of the laser beam is accomplished with an acoustooptic modulator 303 (Model AOM-30 Modulator and Model DE-30X VCO Driver, IntraAction Corporation). Hirschfeld [*Applied Optics*, 15, 1976, 3135] demonstrated that the molecule fluorescein could be efficiently photolyzed with relatively modest laser powers ($\sim$12 kW $cm^{-2}$). These power densities are easily achieved by focusing a low-power continuous wave laser into the capillary column. The experiments described herein employed molecules that are easily labeled with the fluorescein derivative, fluorescein isothiocyanate (FITC). The electrophoretic separation proceeds in much the same way as conventional CE with the effective column length (l) being the distance between the gating beam and the fluorescence detector.

Coupled Capillary Columns to Focus the Electric Field

Figure 4:
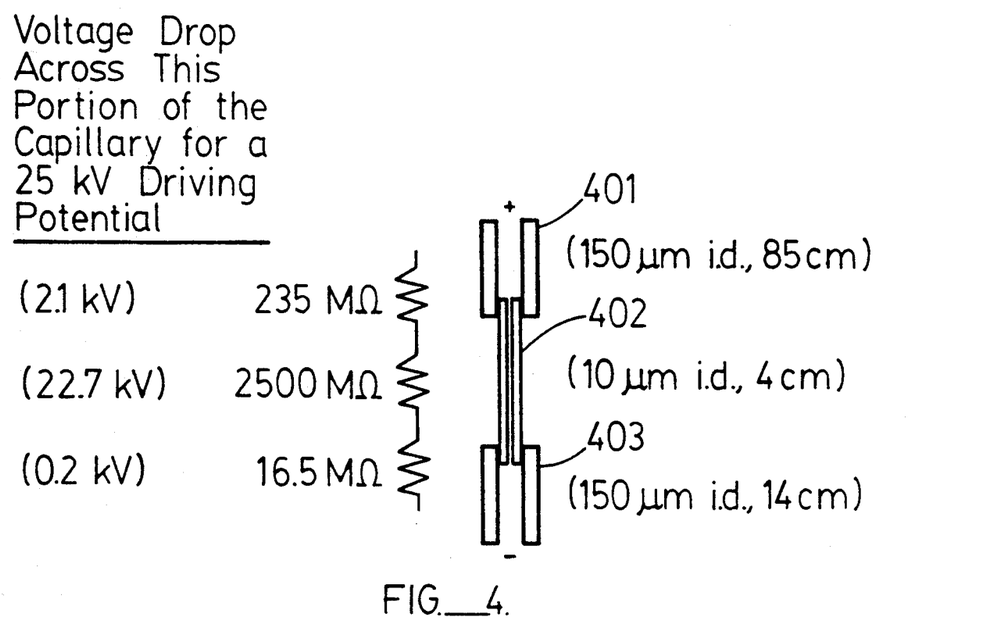
FIG. 4 is a diagram demonstrating the principle of coupling capillaries of different diameters.

It is normally difficult to work in high electric fields with short capillary columns. In particular, spontaneous breakdown in air may occur when the electric field strength exceeds 3000-4000 V $cm^{-1}$. As a result, special attention must be directed toward electrically isolating the buffer reservoirs. However, this problem is solved by coupling capillaries of different diameters to concentrate the electric field into a short section of small diameter capillary. This "coupled-column" technique is illustrated in FIG. 4. In this embodiment, one end of capillary 402 (10 $\mu$m i.d., 4 cm in length) is inserted into capillary 401 (150 $\mu$m i.d., 85 cm in length). The other end of capillary 402 is inserted into capillary 403 (150 $\mu$m i.d., 14 cm in length). The capillaries were bonded at the two connections. The equivalent electrical circuit is shown to the left of the column diagram. Analysis of this circuit indicates that approximately 90% of the voltage drop occurs over the 4 cm length of capillary 402. Consequently, it is possible to generate electric fields in excess of 5000 V $cm^{-1}$ in the short length of capillary 402. Typically, electric fields of only 300 to 400 V $cm^{-1}$ are employed with CE. As discussed previously, this elevated electric field can be used to shorten the time of analysis. However, the overall length of the coupled capillary is the same as the length of typical capillaries used in the traditional CE analysis so problems with isolating the high voltages are minimized.

As discussed previously, Joule heating of the capillary must be minimized if separation efficiency is to be maintained. Capillary diameters between 5 and 15 $\mu$m seem to provide a good compromise between capillary temperature control and ease of use with a fluorescence detector.

Although the above embodiment employs capillaries of different diameters which are bonded together to achieve the electric field focusing effect, other geometries should be feasible. Specifically, it is possible to vary the diameter of the capillary during the drawing process or in etching a capillary of differing diameter in a non-conductive substrate (e.g., silicon wafer). The latter also makes column handling much easier and permits integrated cooling or heating. It is also possible to eliminate either capillary 401 or capillary 403 and employ a capillary means with two sections of different diameters. As long as the sample and electrolyte in a first section have a higher electrical resistance than that of the sample and electrolyte in the second section, the electric field strength in the first section will be higher than that in the second section to achieve a more rapid separation.

Apparatus for Detection and Signal Processing in High Speed CE Employing On-Column Optical Gating and Coupled Capillary Columns As shown in FIG. 3, a small fraction ($\sim$4%) of the laser power is split from the laser beam 304 and directed into the capillary 302 to form a fluorescence detector (the probe beam 106 in FIG. 1). Specifically, a fraction of beam 304 is split by beam splitter 305 into gating beam 105 and probe beam 106. The gating beam is focused onto the capillary by lens 307. The probe beam is focused onto the capillary by mirror 306 and through lens 308. (As shown in FIG. 1, the gating beam and probe beam are focused on different positions on the capillary.) The resulting fluorescence signal is collected with a microscope objective 309 (16x, Melles Griot) and then spectrally isolated with a monochromator (Model H-10, Instruments SA Inc.) and bandpass filter (Omega Optical), together shown as 310. The resulting photon flux is converted to an electrical signal with photomultiplier tube (Model R1527-03, Hamamatsu) and a high speed amplifier (Model 427, Keithley Instruments), together shown as 311. A LabVIEW (National Instruments) program running on the Macintosh II computer acquired the data through a laboratory interface board (Model NB-MIO-16XL-42, National Instruments) configured with a 16-bit analog to digital interface. This same program is used for data processing and storage Peak parameters (theoretical plates, retention time, peak widths, etc.) were derived from statistical moments that were calculated with a second LabVIEW program.

Procedures for Preparing Fluorescently Tagged Molecules

Solutions were prepared in the following manner. First 1 mL of FITC/acetone solution (6.1 mM) is added to 3 mL of 3 mM solution of each amine in a pH 9.2 carbonate buffer. This mixture is allowed to react at room temperature for at least three hours. This mixture is further diluted with the mobile phase (pH 9.2, carbonate buffer) to obtain the desired concentration of labeled product Before use, all solutions were passed through a 0.22 $\mu$l filter to remove particulates.

Sample is introduced into the capillary by electrophoretic migration. Although this sample introduction procedure necessarily selects for those species with the highest electrophoretic mobility, for all molecules studied it was found that the injected amount was adequate for the experiments. Before data collection was initiated, the sample in buffer was passed into the column for several minutes to equilibrate the capillary with the solution. Complex molecules which may be separated with the present invention include charged molecules such a proteins, glycoproteins, peptides, amino acids, and polynucleic acids.

Fluorescent molecules which may be used in connection with this invention are exemplified by fluorescein and fluorescein derivatives, dansyl chloride (5-dimethylaminoonaphthylene-1-sulfonyl chloride) and analogs thereof, coumarin and coumarin analogs, and fluorescamine. Numerous other photobleachable fluorescent molecules are available.

RESULTS FROM THE SEPARATION OF FITC LABELLED ARG, PHE, AND GLU

Figure 5:
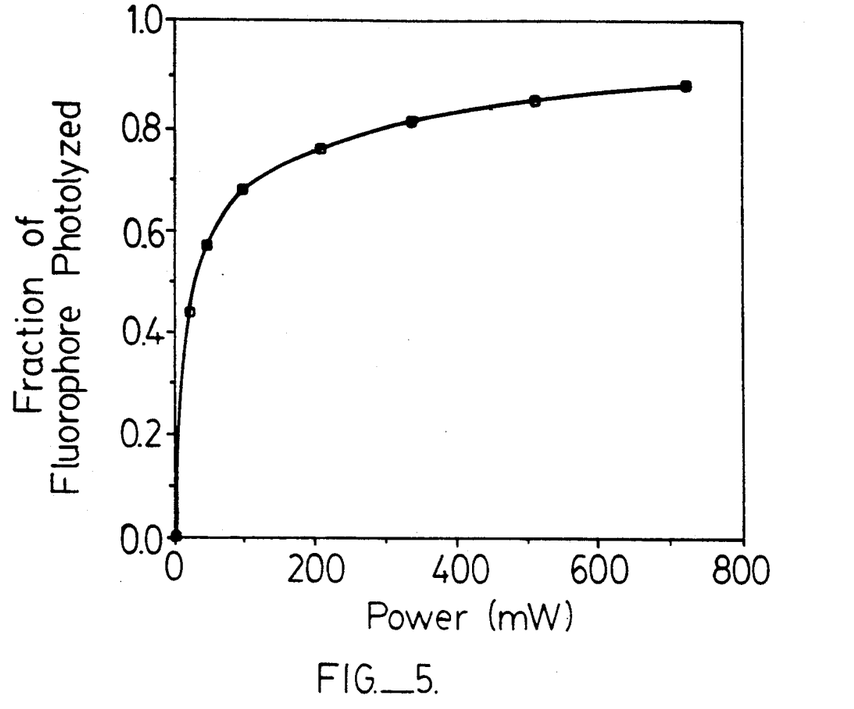
FIG. 5 is a plot showing the effect of gating beam power on the fraction of fluorophore photolyzed.

The success of on-column optical gating relies upon its ability to efficiently photodegrade the fluorescently-labeled compound as it passes through the gating beam. To assess the degree to which complete photobleaching was observed, a bare fused silica capillary (10 $\mu$m i.d.) was employed with the inventive apparatus described. FITC labeled arginine was forced through the capillary at a constant velocity (0.19 cm s$^{-1}$). The relationship between probe beam power and the fraction of the fluorophore photolyzed is illustrated in FIG. 5. These data suggest that at least two processes are involved in the photolysis of fluorescein. The first mechanism is fast and irreversible. This accounts for the rapid drop in fluorescence intensity observed at low laser powers. The second mechanism is less sensitive to laser power and accounts for the elevated fluorescence levels observed even at high laser powers. Unfortunately, this persistent fluorescence introduces a background upon which all the signals must be observed. Not surprisingly, this background increased the noise which limits the dynamic range and precision of the measurements. However, there is no reason to believe that other fluorophores would suffer from these same limitations.

Figure 6:
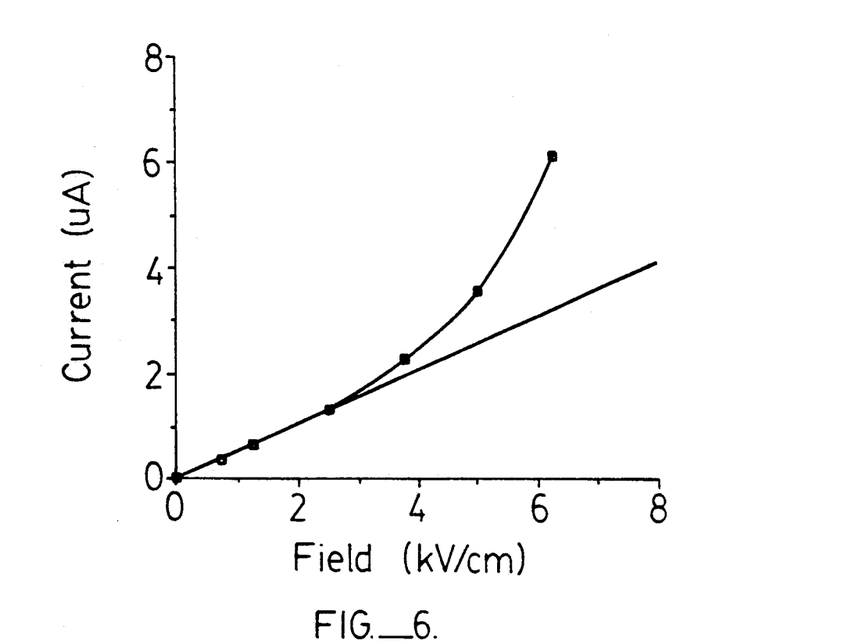
FIG. 6 is a plot of the current passing through the coupled capillary as a function of the electric field in the small diameter capillary. The buffer solution was 30 mM carbonate at pH 9.2.
Figure 7:
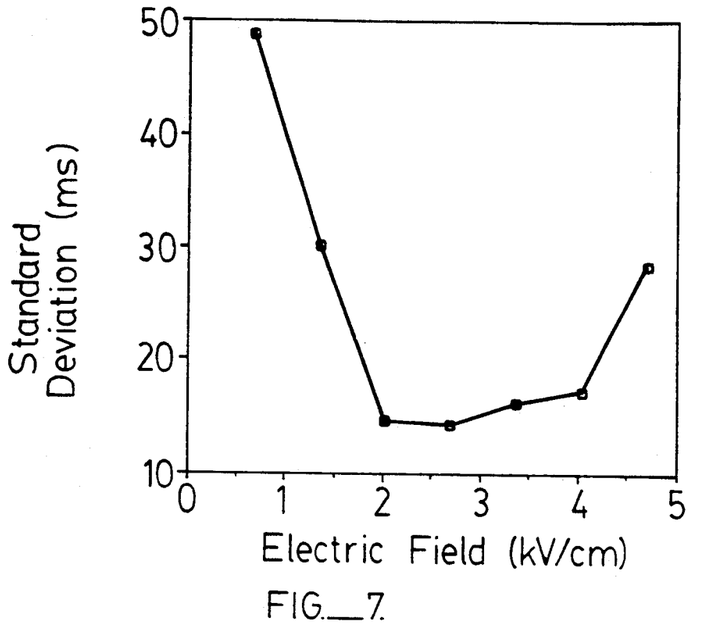
FIG. 7 is the graph of standard deviation of the fluorescein peak as a function of the electric field in a small diameter capillary. Column length (l) was 1.2 cm and the buffer was the same as listed in FIG. 6. The electric field in the small diameter capillary was maintained at 2.7 kV cm$^{-1}$.

FIG. 6 shows the measured current passing through the coupled capillary column as a function of the electric field in the short capillary. Significant deviations from linear behavior are observed by the time the field strength has reached 3 kV cm$^{-1}$. This behavior is indicative of Joule heating of the buffer. FIG. 7 supports this hypothesis by plotting the temporal standard deviation of the sample zone as a function of the electric field. A minimum zone width is observed when the applied voltage is 2.0 kV cm$^{-1}$. This problem can be partially overcome by reducing the current passing through the capillary. This is easily accomplished by lowering the concentration of the supporting electrolyte in the buffer or by further reducing the diameter of the capillary.

Figure 8:
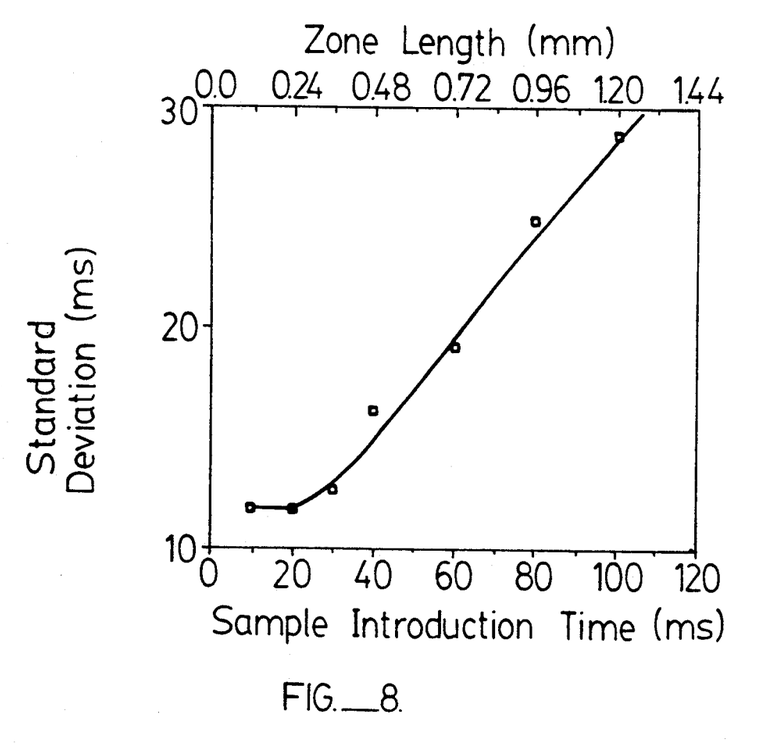
FIG. 8 is the graph of standard deviation of the FITC labeled arginine peak as a function of the sample introduction time. The buffer was the same as listed in FIG. 6.

In FIG. 8 the temporal standard deviation of the peak for FITC labeled arginine is plotted as a function of the sample introduction time (the time the "gating" laser beam is deflected away from the capillary) for a capillary with a length (l) of 1.2 cm and an electric field of 3.3 kV cm$^{-1}$. These data demonstrate that temporally small sample zones must be injected into the capillary to obtain a minimum peak width. As illustrated in FIG. 8, the sample introduction time is preferably less than about 40 milliseconds.

Figure 9:
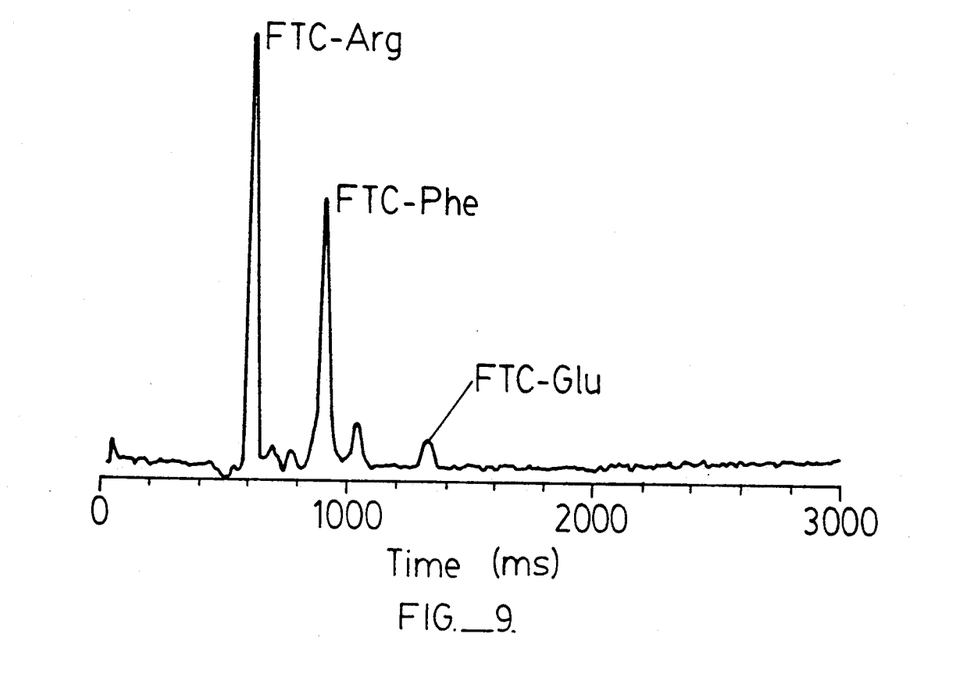
FIG. 9 is an electropherogram of a mixture of FITC labeled amino acids. Sample introduction time was 40 ms. The buffer was the same as listed in FIG. 6. Analyte concentrations are 10 μM for each species.

FIG. 9 shows the electropherogram acquired when a solution containing FITC derivatives of three amino acids (Arg, Phe, Glu) was introduced into the instrument. For this analysis, the distance between the "gating" and the "probe" beams was 1.2 cm. The electric field was maintained at 3.3 kV cm$^{-1}$. The elution time for these three species are 0.62, 0.91 and 1.33 seconds respectively. The theoretical plates for these peaks ranged between 5000 and 7000.

Figure 10:
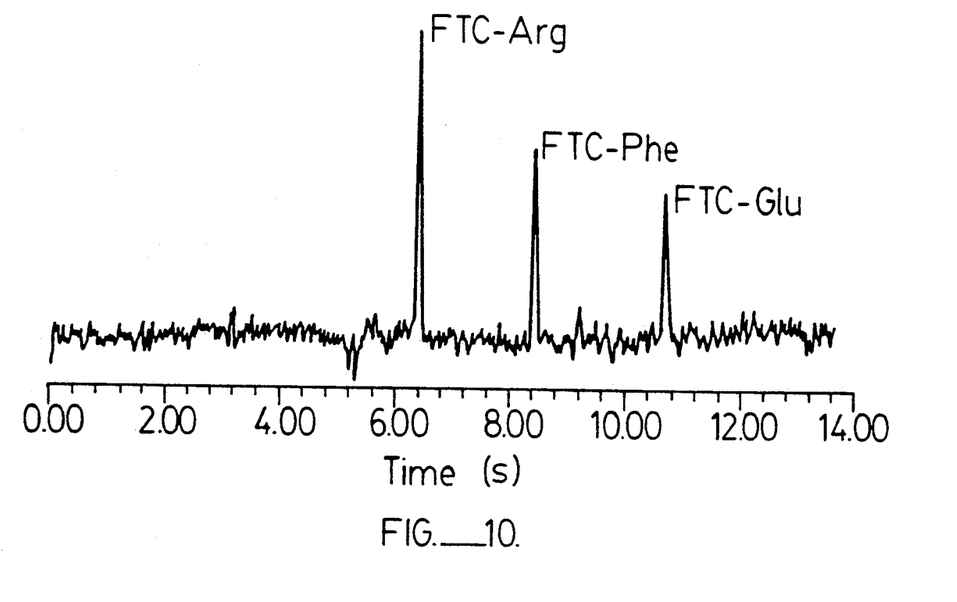
FIG. 10 is an electropherogram of a mixture of FITC labeled amino acids Sample introduction time was 50 ms. Analyte concentrations are 8 μM for each species. The buffer solution was the same as listed in FIG. 6.

Separation of the amino acids (Arg, Phe, Glu) had been reported by Cheng and Dovichi [Science, 242, 1988, 562]. In that report, the elution time for the amino acids ranged between 13 and 24 minutes with peak efficiencies of approximately 400,000 theoretical plates. Thus, a decrease in separation efficiency accompanies the increase in overall speed of analysis Heat buildup in the capillary likely has contributed to some of the width of the peak observed in FIG. 9. The inventive capillary device can accommodate electric field strengths up to at least 5000 V/cm$^{-1}$. Moreover, with integrated (i.e., active) cooling significantly higher fields can be accommodated. In principle, reducing this excess heat should allow even higher separation efficiencies to be obtained To regain some of the efficiency sacrificed the operating conditions were modified. FIG. 10 shows the electropherogram obtained when these same compounds were electromigrated in a field of 1750 V cm$^{-1}$ over a distance of 4 cm. The efficiencies of the three peaks ranged from 70,000 to 90,000 theoretical plates which corresponds to approximately $2 \times 10^6$ plates per meter and a HETP of 0.5 $\mu$m. Arginine was found to be separated at a rate equivalent to 12,000 theoretical plates per second Equally important, the peak capacity of the electropherogram has been dramatically increased.

Application of High Speed CE with Multiplex Separations

Multiplex separation techniques provide an alternative to the batch separation mode (single injection input signal) employed in the vast majority of separation procedures. Both techniques produce essentially identical information (i.e., data about individual components in a mixture). However, the multiplex mode of operation can provide some very important advantages when the analyte to be determined is near the detection threshold or when transient events must be monitored [Annino and Grushka, J. Chromatogr. Sci., 14, 1976, 265; Phillips, Anal. Chem., 52, 1980, 468A].

In the multiplex separation procedure, multiple sample injections are made into the carrier stream. Ideally, each injection results in a separation of the mixture components just as in the single injection mode. However, peaks from these separations can be strongly overlapped at the detector and are therefore not directly interpretable by the analyst. However, if the injection function is known, the separation information can be recovered (e.g., by cross-correlation or deconvolution). The primary advantage of this detection mode is that sample throughput is enhanced which in principle will reduce the limits of detection for any given species Furthermore, because a separation does not have to be complete before the next injection is made, monitoring of transient signals can be accomplished with relative ease.

Several problems have inhibited the development of multiplex separation procedures for chemical analysis. Most multiplex methods employ computers for experiment control and data interpretation. Only recently has the widespread availability of powerful personal computers overcome this problem. A more fundamental problem, particularly for chromatographic separations, is loading of the stationary phase by the multiple sample injections. The resulting non-linear partitioning of the solute between the stationary and the mobile phase can make quantitative interpretation of the recorded signal difficult if not impossible. To its advantage, CE does not involve the partitioning of the solute between phases, and therefore, is not susceptible to this problem. The "high-speed" CE instrument described above is particularly well suited for this application because of the rapid analysis times and simplicity of making multiple injections onto the column. Although multiplex separations perform particularly well in electrophoresis, multiplex chromatographic systems employing the inventive instrumentation should also yield good results. This is particularly the case with gas chromatography where equilibrium between the mobile and stationary phases is achieved relatively quickly.

Figure 11:
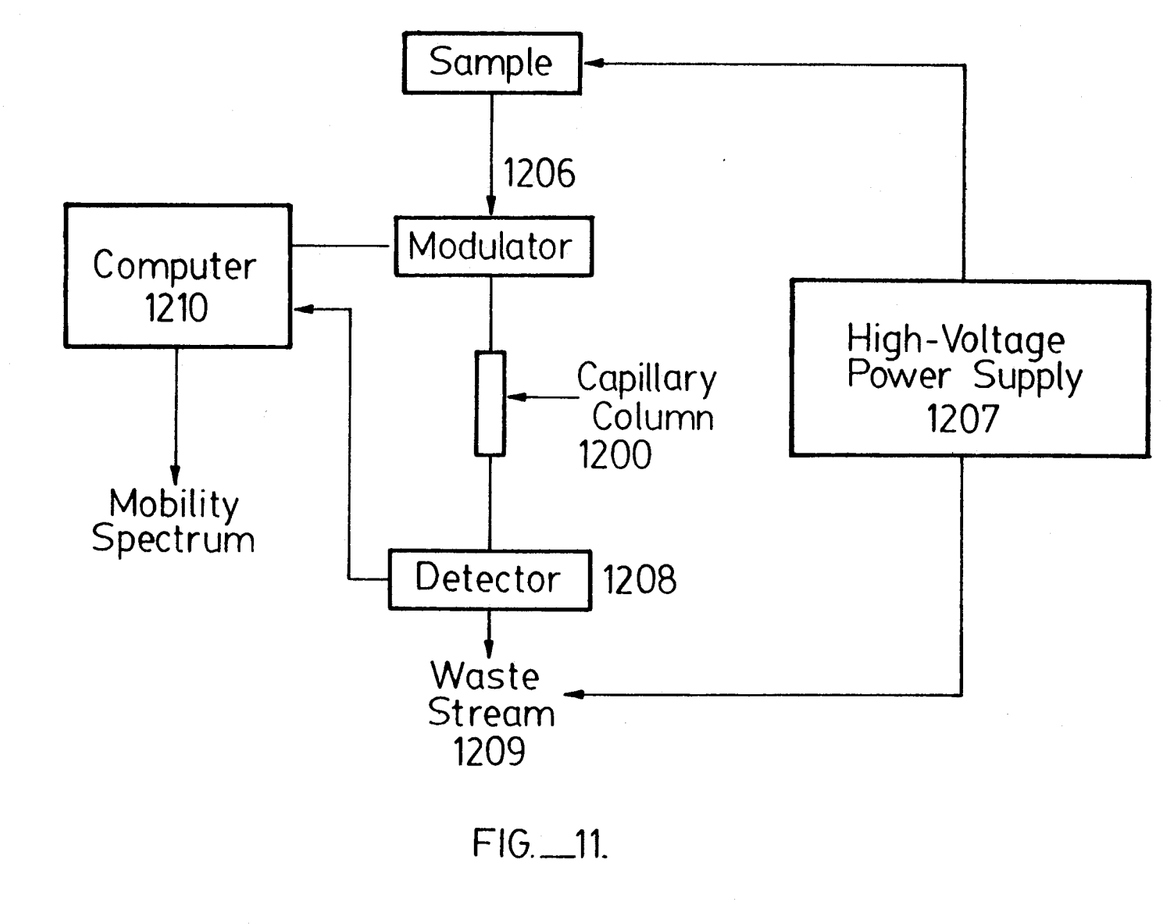
FIG. 11 shows a block diagram of a multiplex capillary electrophoresis apparatus.

Multiplex procedures provide a unique method whereby the limits of detection of time resolution of a separation can be enhanced. FIG. 11 shows a block diagram of a multiplex capillary electrophoresis apparatus. In this embodiment, modulation device 1206 provides multiple sample injections of the analyte into capillary column 1200 where it is separated. Modulating device 1206 can comprise the above-described inventive on-column optical gating employing a laser or other conventional means such as microswitching. The effluent exits via waste stream 1209. Computer 1210 generates a pseudo-random modulation waveform which is used to control sample introduction into the capillary. A voltage power supply source 1207 maintains a high potential for separation. A detector 1208 is used to record the passage of the analyte peaks as they elute from the column. The detector output is digitized and stored by the computer. After data collection is complete, the mobility spectrum is determined by cross-correlating the modulation waveform with the detector output. The cross-correlation is performed using the above-referenced LabVIEW program.

The multiplex technique described above employs the on-column optical gating device in an "on" and "off" mode, which can be represented as square waves. However, multiplex separation can also be accomplished if samples are introduced continuously and in varying concentrations, which can be represented, for example, as a sine wave, or a pseudo-random waveform. Where the passage of analyte peaks from different samples overlap, a pseudo-random modulation injection waveform (for example, pseudo-random pattern of turning the laser on and off) will enable the peaks to be identified using the LabVIEW Program Data Recovery techniques employing conventional pseudo-random waveforms.

It is to be understood that while the invention has been described above in conjunction with preferred specific embodiments, the description and examples are intended to illustrate and not limit the scope of the invention, which is defined by the scope of the appended claims.

It is claimed:

1. A separation apparatus comprising:
   a capillary column;
   input means for introducing a sample into the capillary column;
   means positioned along a section of the column for irradiating a portion of the sample in said section to affect a detectable characteristic of said portion wherein at lest one component separated for the portion upon subsequent separation is distinguishable from the same component separated from the rest of the sample upon subsequent separation by means of said characteristic;
   means for causing separation of the sample into sample components in the column and for causing the sample component to migrate along the column; and
   detection means located along the column downstream from the affecting means for detecting the separated components by detecting said characteristic.

2. An apparatus as in claim 1 wherein the irradiating means comprises gating means for intermittently focusing a laser beam at the sample in the capillary column.

3. An apparatus as in claim 2 wherein the detection means comprises means for detecting fluorescent tagged sample components, wherein the sample is tagged with a fluorescent material prior to separation and wherein the laser beam photodegrades a selected portion of the fluorescent tagged sample such that parts of separated sample components originating from the photodegraded portion of the sample are undetectable by the detection means.

4. An apparatus as in claim 3 wherein the means for detecting fluorescent tagged sample components comprises means for inducing fluorescence by influence of laser radiation.

5. An apparatus as in claim 4 wherein the means for causing separation comprises means for causing electrophoretic separation.

6. An apparatus as in claim 5 wherein electrophoretic separation takes place along a section less than 10 cm of the capillary column and the means for causing separation comprises means for applying a electric potential of greater than 1000 V/cm.

7. A separation apparatus comprising:
   a capillary column;
   input means for introducing a sample into the capillary column;
   means positioned along the column for irradiating a portion of the sample in said section to affect a detectable characteristic of the sample, thereby modulating the sample into a sequence of segment according to a predetermined pattern, wherein components separated from the sequence of segments are rendered detectable by said characteristic;
   means for causing separation in the column of segments that contain detectable sample components, and for causing the sample components to migrate a long the column;
   detection means located along the column downstream form the irradiating means for detecting separated sample components from the segments by detecting said characteristic, said detection means comprising means for generating an output; and
   multiplex means for controlling multiplex detection of separated components originating from different segments, said multiplex means further comprising means for cross correlating the predetermined pattern with the detection means output so that the particular segment in the sequence from which a detected separated component originated can be determined despite overlaps of the sample components from different segments.

8. An apparatus as in claim 6 wherein said irradiating means comprises means for marking each segment int the sequence with a different waveform and further comprises means for controlling the detection means to identify the waveform of each detectable sample component thereby determining the originating segment of each detecting sample component.

9. An apparatus as in claim 8 wherein said marking means marks at least one segment in the sequence with a waveform that is represented by a sine wave.

10. An apparatus as in claim 8 wherein said marking means marks at least one segment in the sequence with a pseudo-random waveform.

11. The apparatus as in claim 8 wherein the marking means comprises means for intermittently focusing a laser beam at the sample in the capillary according to a predetermined pseudo-random waveform.

12. An apparatus as in claim 11 wherein the detection means comprises means for detecting fluorescent tagged sample components, wherein the sample includes a fluorescent material and wherein the laser beam photodegrades a portion of the fluorescent tagged sample in each segment such that parts of separate sample components originating from the photodegraded portion of the sample are undetectable by the detection means.

13. An apparatus as in claim 12 wherein the means for marking the segments comprises means for controlling the irradiating means to selectively, in accordance with the respective waveforms, cause certain segments to be substantially undetectable by the detection means upon separation thereby marking the remaining selected segments.

14. The apparatus as in claim 13 wherein the means for detecting fluorescent tagged sample components comprises means for inducing fluorescence by influence of laser radiation.

15. The apparatus as in claim 14 wherein said separation means comprises means for causing electrophoretic separation.

16. The apparatus as in claim 15 wherein electrophoretic separation takes place along a section less than 10 cm of the capillary column and the means for causing separation comprises means for applying an electric potential of greater than 1000 V/cm.

17. A separation apparatus comprising:
a capillary channel;
mean for causing a sample to migrate and separate in the channel;
means for continuously providing a sample to said channel, so that the sample entering the channel migrates and undergoes separation into components in the channel;
a detector positioned along a section of the channel for interrogating separated components migrating past said section;
gating means located upstream of the detector along the channel for modulating the sample to cause at least one component associated with a portion of the sample to have a different detectability form the same component associated with the rest of the sample by said detector, wherein said gating means irradiates a portion of the sample in said section to affect a detectable characteristic of a portion of the sample.

18. The apparatus of claim 17, wherein said gating means photodegrades said portion of the sample.

19. A separation method employing a capillary channel, comprising:
causing a sample to migrate and separate in the channel into its components;
detecting at a position along the channel separated components migrating past said position;
modulating the sample at a location upstream of the position along the channel to cause at least one component associated with a first portion of the sample to be less detectable than the same component associated with a second portion of the sample in the detecting step.

20. The method of claim 19, said first portion of the sample including a first section and a second section, said second portion located between said first section and said second section, said modulating step being such that it renders the at least one component associated with said first and second sections less detectable by said detecting step than the same component associated with the second portion of the sample located in the channel between the first and second sections, said second portion forming a plug of sample detectable by the detecting step.

21. The method of claim 19, wherein said modulating step includes the step of irradiating the first portion of the sample.

22. The method of claim 21, wherein said irradiating step photodegrades said first portion of the sample.

* * * * *

UNITED STATES PATENT AND TRADEMARK OFFICE
CERTIFICATE OF CORRECTION

PATENT NO. : 5,269,900
DATED : December 14, 1993
INVENTOR(S) : Jorgenson et al.

Page 1 of 2

It is certified that error appears in the above-indentified patent and that said Letters Patent is hereby corrected as shown below:

| | |
|---|---|
| Column 9, line 67, in Claim 1: | Replace "lest" with --least-- and "for" with --from-- |
| Column 10, line 6, in Claim 1: | Replace "component" with --components-- |
| Column 10, line 43, in Claim 7: | Replace "segment" with --segments-- |
| Column 10, line 51, in Claim 7: | Replace "a long" with --along-- |
| Column 10, line 53, in Claim 7: | Replace "form" with --from-- |
| Column 10, line 67, in Claim 8: | Replace "An" with --The-- and "6" with --7-- |
| Column 10, line 68, in Claim 8: | Replace "int" with --in-- |
| Column 11, line 5, in Claim 8: | Replace "detecting" with --detected-- |
| Column 11, line 6, in Claim 9: | Replace "An" with --The-- |
| Column 11, line 9, in Claim 10: | Replace "An" with --The-- |
| Column 11, line 16, in Claim 12: | Replace "An" with --The-- |

UNITED STATES PATENT AND TRADEMARK OFFICE
CERTIFICATE OF CORRECTION

PATENT NO. : 5,269,900
DATED : December 14, 1993
INVENTOR(S) : Jorgenson et al.

It is certified that error appears in the above-indentified patent and that said Letters Patent is hereby corrected as shown below:

Column 11, line 21, in Claim 12: Replace "separate" with --separated--

Column 11, line 25, in Claim 13: Replace "An" with --The--

Column 11, line 46, in Claim 17: Replace "mean" with --means--

Column 12, line 11, in Claim 17: Replace "form" with --from--

Signed and Sealed this

Thirty-first Day of May, 1994

Attest:

BRUCE LEHMAN

Attesting Officer

Commissioner of Patents and Trademarks